(12) United States Patent
Gee et al.

(10) Patent No.: US 11,478,329 B2
(45) Date of Patent: Oct. 25, 2022

(54) MAGNETIC LATCH FOR A SURGICAL ROBOTIC SYSTEM

(71) Applicant: Verb Surgical Inc., Santa Clara, CA (US)

(72) Inventors: Jacob S. Gee, Cincinnati, OH (US); Robert T. Wiggers, Belmont, CA (US)

(73) Assignees: Verb Surgical Inc., Santa Clara, CA (US); Maquet GmbH, Rastatt (DE)

( * ) Notice: Subject to any disclaimer, the term of this patent is extended or adjusted under 35 U.S.C. 154(b) by 409 days.

(21) Appl. No.: 16/814,887

(22) Filed: Mar. 10, 2020

(65) Prior Publication Data
US 2021/0282890 A1 Sep. 16, 2021

(51) Int. Cl.
| | | |
|---|---|---|
| *A61B 17/00* | (2006.01) | |
| *A61B 90/57* | (2016.01) | |
| *A61B 34/30* | (2016.01) | |
| *F16B 1/00* | (2006.01) | |
| *A61G 13/10* | (2006.01) | |
| *B25J 9/00* | (2006.01) | |
| *A61B 34/00* | (2016.01) | |

(52) U.S. Cl.
CPC .............. *A61B 90/57* (2016.02); *A61B 34/30* (2016.02); *A61G 13/101* (2013.01); *B25J 9/0009* (2013.01); *F16B 1/00* (2013.01); *A61B 34/70* (2016.02); *A61B 2017/00477* (2013.01); *A61B 2017/00876* (2013.01); *A61B 2090/571* (2016.02); *F16B 2001/0035* (2013.01)

(58) Field of Classification Search
CPC ......... A61B 34/70; A61B 90/57; A61B 34/30; A61B 2090/571; A61B 2017/00477; A61B 2017/00876; B25J 9/0009
USPC ...................... 606/1; 248/206.5, 309.4, 683
See application file for complete search history.

(56) References Cited

U.S. PATENT DOCUMENTS

2020/0138534 A1* 5/2020 Garcia Kilroy ...... A61G 13/101
2022/0039909 A1* 2/2022 Abbott .................... A61B 90/57
2022/0125461 A1* 4/2022 Black ............. A61B 17/320092

* cited by examiner

*Primary Examiner* — Todd M Epps
(74) *Attorney, Agent, or Firm* — Womble Bond Dickinson (US) LLP

(57) ABSTRACT

A surgical robotic system that includes a surgical table that is configured to hold a patient and a magnetic latch. The magnetic latch has a ferromagnetic plate, a permanent magnet that produces a first magnetic field and that attracts the ferromagnetic plate to thereby couple a robotic arm to the surgical table, and a cancelling coil, which when energized, produces a second magnetic field that opposes the first magnetic field to thereby uncouple the robotic arm from the surgical table.

20 Claims, 7 Drawing Sheets

MAGNETIC LATCH FOR A SURGICAL ROBOTIC SYSTEM

FIELD

An embodiment of the disclosure relates generally to surgical robotic systems, and more specifically to a surgical robotic system that includes a magnetic latch for magnetically coupling a robotic arm to a surgical table. Other embodiments are also described.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures can then be performed by using the introduced surgical tools, with the visualization aid provided by the camera.

Generally, MIS provides multiple benefits, such as reduced patient scarring, less patient pain, shorter patient recovery periods, and lower medical treatment costs associated with patient recovery. MIS can be performed with surgical robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. Thus, a surgical robotic arm can assist in performing surgery.

Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

SUMMARY

A surgical robotic system may include a surgical robotic manipulator, for example a surgical robotic arm (or robotic arm) that is coupled to a fixed structure such as a surgical table. In particular, the robotic arm may connect to a connection that is a part of the surgical table. In conventional solutions, connection may be a structure that locks one end of the robotic arm into place using one or more holding mechanisms, such as a bolt. This end of the robotic arm may be bottom heavy in order to support the remainder of the arm. In addition, this end may be composed of flexible components (e.g., joints) in order to provide one or more degrees of freedom to the arm. These conventional systems have drawbacks. For example, since the end of the robotic arm is heavy (e.g., composed of heavy material), the robotic arm may be heavy and cumbersome for someone to remove from the table and carry away. Also, removing the robotic arm from the surgical table may be complicated and time consuming. For instance, in order to release the arm from the table, the holding mechanisms may need to be physically removed before lifting the robotic arm out from the table's connection. Removing (or adding) these holding mechanisms may require special tools, and several users (e.g., one user to release the mechanism and another user to hold the arm). In addition, the flexible components may result in poor system performance. Thus, there is a need for a compact and light magnetic latch that allows a user to easily add and remove a robotic arm from a surgical table, and also provides a rigid connection point to prevent unintentional movement, shifting, or rotating of the robotic arm while it is in place.

The present disclosure provides a magnetic latch that enables a robotic arm of a surgical robotic system to be coupled to a surgical table with the use of a permanent magnet. For example, the magnetic latch includes a ferromagnetic plate (e.g., a steel plate) and the permanent magnet, which produces a first magnetic field and that attracts the ferromagnetic plate to thereby couple the robotic arm to the surgical table. Specifically, the magnetic latch may include a connecting link of the robotic arm and a table link that is rigidly coupled to the surgical table. The magnetic components may than be integrated into the links. For instance, the magnet may be integrated with the table link, while the ferromagnetic plate may be integrated with the connecting link of the robotic arm. When the links are joined together, the first magnetic field produced by the permanent magnet attracts the ferromagnetic plate, causing the links to latch together thereby coupling the robotic arm to the surgical table. Thus, unlike conventional solutions that are flexible at the connection point, the magnetic latch rigidly connects the (connecting link of the) robotic arm to the surgical table (via the table link).

The magnetic latch may also include a canceling coil (e.g., an electromagnet), that allows a user to uncouple the robotic arm from the surgical table. Specifically, when the canceling coil is energized, the coil produces a second magnetic field that opposes the first magnetic field to thereby uncouple the robotic arm from the surgical table. As a result, when energized, a user may pull the connecting link of the robotic arm a part from the table link, since the magnet's magnetic field is reduced by the second magnetic field. Thus, the magnetic latch allows a user to add and/or remove a robotic arm from the surgical table with ease. For example, unlike conventional systems that may require special tools to secure the arm (e.g., with bolts), no special tools are required to add or remove the arm from the table. Furthermore, the components of the magnetic latch may be distributed between the links in order to reduce the weight of the robotic arm. In particular, the permanent magnet may be heavier than the ferromagnetic plate. As a result, the permanent magnet may reside within the table link, while the plate resides in the connecting link of the robotic arm, thus making it easier for a user to handle the arm.

The above summary does not include an exhaustive list of all embodiments of the disclosure. It is contemplated that the disclosure includes all systems and methods that can be practiced from all suitable combinations of the various embodiments summarized above, as well as those disclosed in the Detailed Description below and particularly pointed out in the claims. Such combinations may have particular advantages not specifically recited in the above summary.

BRIEF DESCRIPTION OF THE DRAWINGS

The embodiments are illustrated by way of example and not by way of limitation in the figures of the accompanying drawings in which like references indicate similar elements. It should be noted that references to "an" or "one" embodiment of this disclosure are not necessarily to the same embodiment, and they mean at least one. Also, in the interest of conciseness and reducing the total number of figures, a given figure may be used to illustrate the features of more than one embodiment, and not all elements in the figure may be required for a given embodiment.

DETAILED DESCRIPTION

Several embodiments of the disclosure with reference to the appended drawings are now explained. Whenever the shapes, relative positions and other embodiments of the parts described in a given embodiment are not explicitly defined, the scope of the disclosure here is not limited only to the parts shown, which are meant merely for the purpose of illustration. Also, while numerous details are set forth, it is understood that some embodiments may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
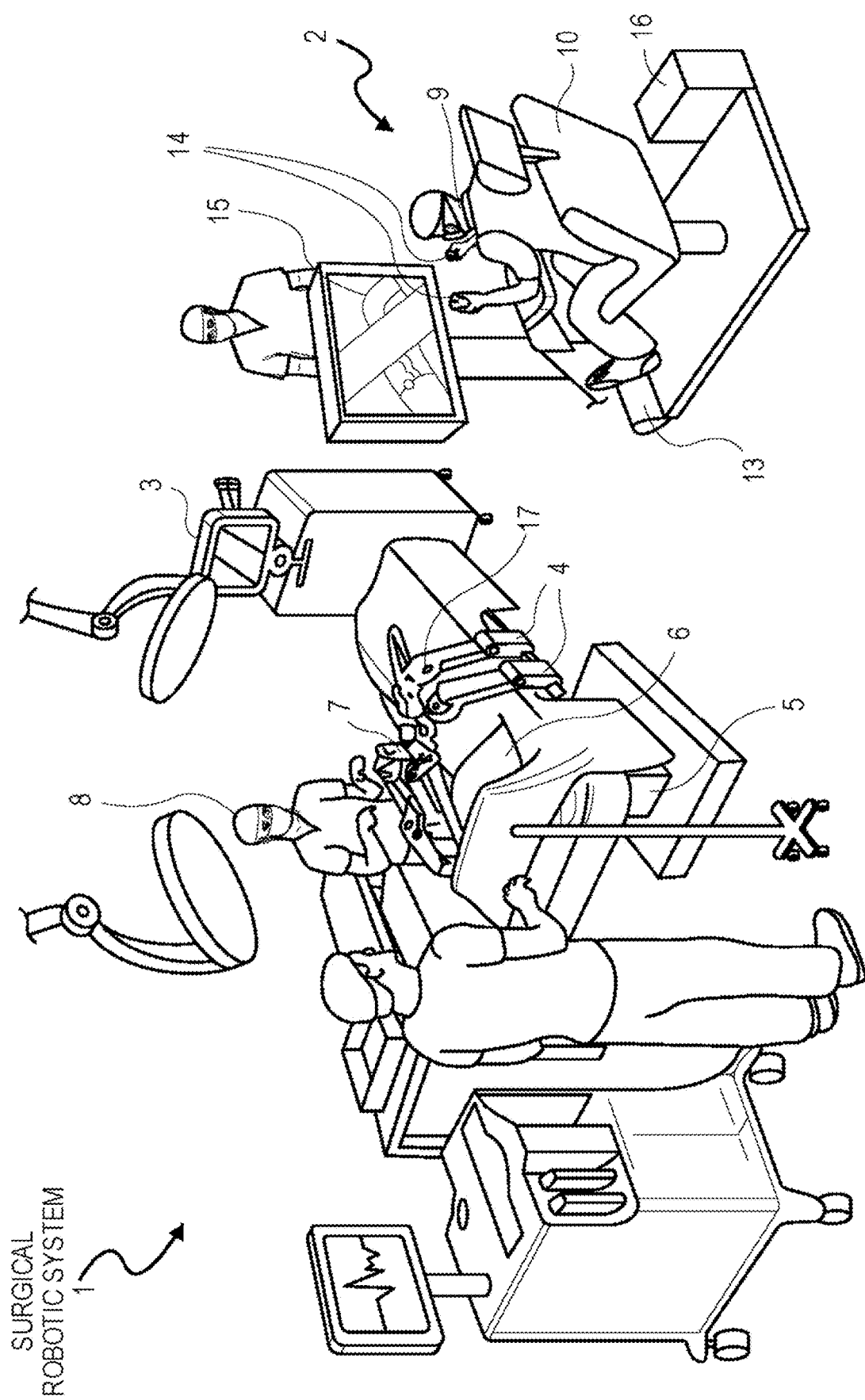
FIG. 1 shows a pictorial view of an example surgical robotic system in an operating arena.

FIG. 1 shows a pictorial view of an example surgical robotic system 1 in an operating arena. The robotic system 1 includes a user console 2, a control tower 3, and one or more surgical robotic arms 4 at a surgical robotic table (or surgical table) 5. In one embodiment, the arms 4 may be mounted to a table or bed on which the patient rests as shown in the example of FIG. 1, or they may be mounted to a cart separate from the table or bed. In one embodiment, at least some of the arms 4 may be configured differently. For example, at least some of the arms may be mounted on a ceiling, sidewall, or in another suitable structural support. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices (handheld UIDs) 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilising the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 (or driving mechanism) in the robotic system 1. The UID 14 may be communicatively coupled to the rest of the robotic system 1, e.g., via a console computer system 16 (or host). The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 or driving mechanism may include one or more actuators and/or one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some embodiments, the communication between the surgical robotic table 5 and the user console 2 may be through a control tower 3, which may translate user commands that are received from the user console 2 (and more particularly from the console computer system 16) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable ones of a variety of data communication protocols, such as BLUETOOTH protocol. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
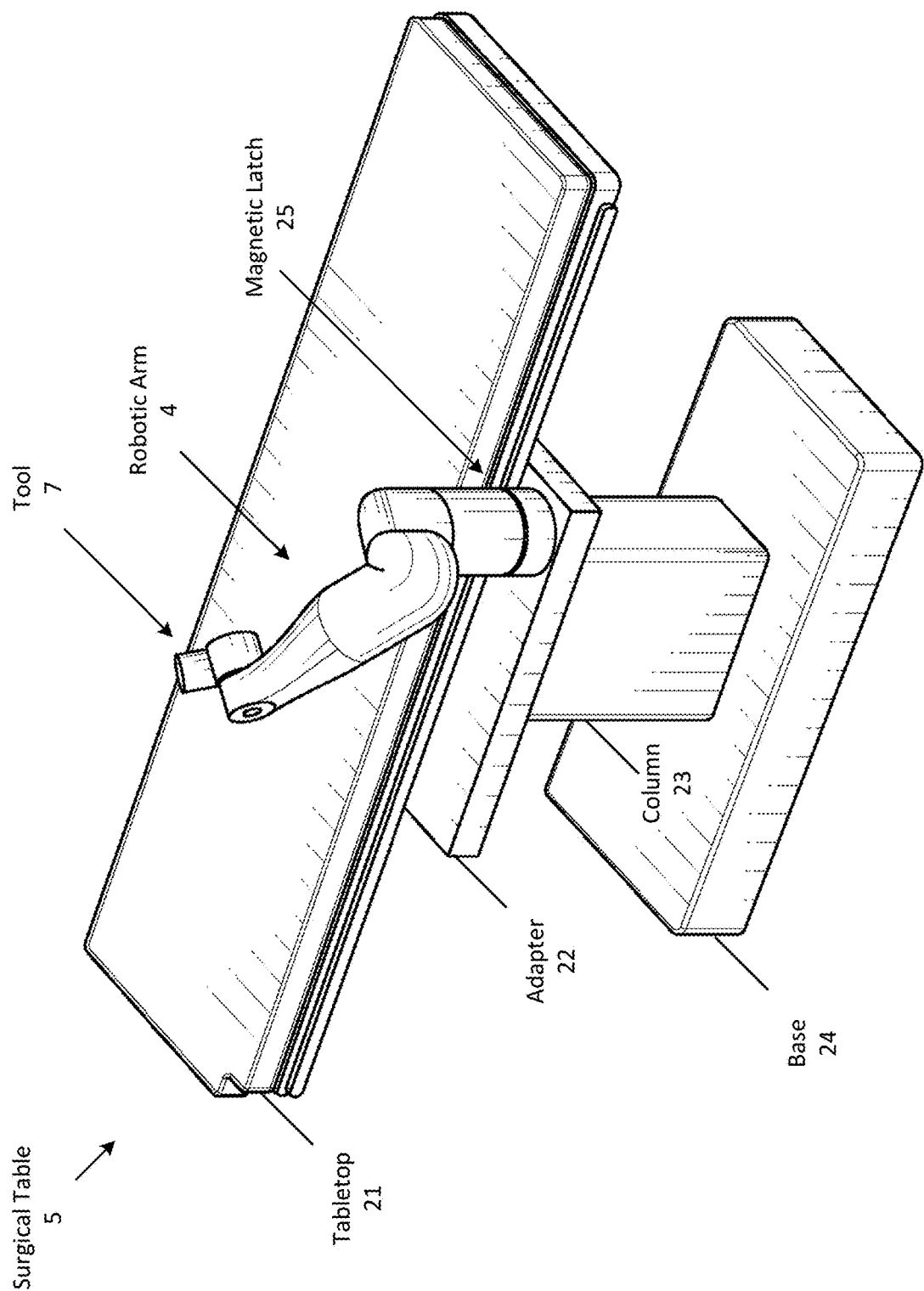
FIG. 2 shows an example of a magnetic latch that is coupling a robotic arm to a surgical table of a surgical robotic system according to one embodiment.

FIG. 2 shows an example of a magnetic latch that is coupling a robotic arm to a surgical table of a surgical robotic system according to one embodiment. As shown in this figure, the surgical table 5 includes a tabletop 21, an adapter 22, a table support or column 23, a table base or base 24, and a magnetic latch 25 that is coupling the robotic arm 4 to the surgical table 5. More specifically, the magnetic latch is coupling the robotic arm to the adapter 22. The surgical table is configured to hold a patient. In particular, the tabletop has an upper surface on which a patient can be disposed during a surgical procedure. The tabletop is disposed on the adapter 22, which is a structure that is configured to support one or more robotic arms. Thus, in one embodiment, each robotic arm may be permanently, semi-permanently, or releaseably (or removeably) coupled to the adapter 22 via the magnetic latch 25 or by another connecting mechanism. In one embodiment, one or more robotic arms may be coupled (e.g., via a magnetic latch 25) to another component of the surgical table. For instance, a robotic arm may be coupled to the column 23 or the tabletop 21.

The adapter is disposed on the column 23, which can be, for example a pedestal, at a suitable height above the floor. In one embodiment, the column may provide for movement of the table top (and adapter) in desired number of degrees of freedom (e.g., moving in a vertical direction at a particular height above the floor). The column 23 is mounted to the base 24, which can be fixed to the floor of the operating room, or can be movable relative to the floor, e.g., by use of wheels on the base. In one embodiment, the surgical table 5 may include more or less components as described herein. For example, the surgical table may include two or more robotic arms 4, each with a particular medical instrument (or surgical tool) 7 (removeably) coupled to a distal end of the arm in order to perform a desired function. Each (or at least some) of the arms may be magnetically coupled to the adapter via a separate magnetic latch. As another example, the surgical table 5 may not include an adapter 22. In this case, the robotic arms may be coupled to the top surface (or bottom surface) of the tabletop 21 (and/or the column 23) via the magnetic latch.

Figure 3:
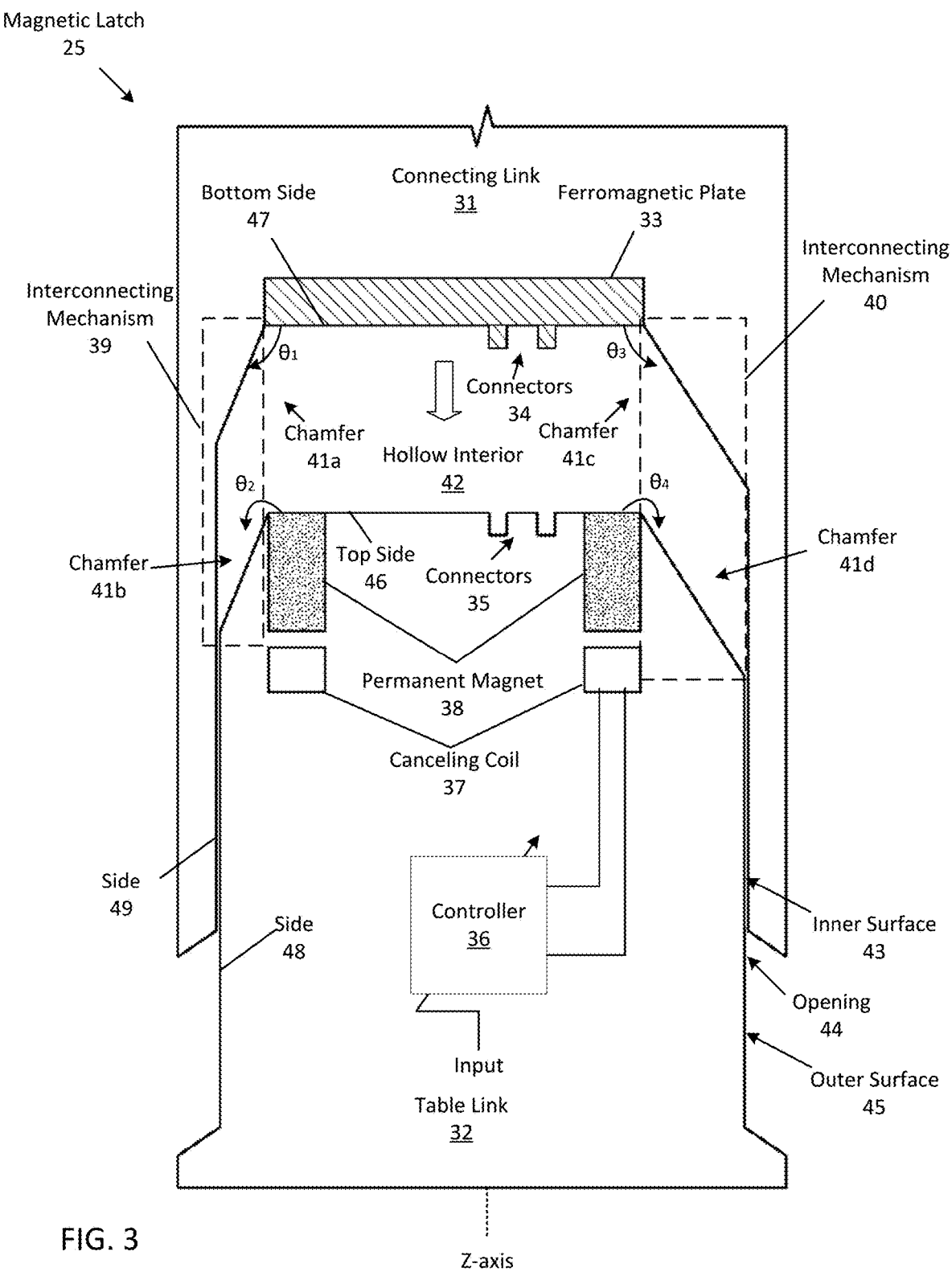
FIG. 3 shows a cross-sectional view of the magnetic latch in which the robotic arm is being attached to the surgical table according to one embodiment.

FIG. 3 shows a cross-sectional view of the magnetic latch in which the robotic arm is being attached to the surgical table according to one embodiment. Specifically, this figure illustrates a cross-section of the magnetic latch 25, while the robotic arm 4 is being (magnetically) coupled to the surgical table. As illustrated, the magnetic latch 25 includes a table link 32 and a connecting link 31. In one embodiment, the table link 32 is fixedly or rigidly coupled to the (e.g., adaptor 22 of the) surgical table 5, meaning that the table link 32 cannot move with respect to the surgical table. In another embodiment, the table link 32 may be configured to move (e.g., rotate with respect to a longitudinal Z-axis that runs through a center of the table link 32). In some embodiments, the table link may be removeably coupled to the surgical table. The connecting link 31 is coupled to (e.g., a proximal end of the) robotic arm 4. In other words, the connecting link is coupled to an end of the robotic arm that is opposite to a (distal) end of the robotic arm that is configured to hold the one or more surgical tools 7 used to perform a surgery. In one embodiment, the connecting link may be coupled to the robotic arm 4 via a joint (not shown). In one embodiment, the joint is configured to rotate or move in one more degrees of freedom.

The connecting link 31 is a structure that is at least partially tubular-shaped with an opening 44 that opens into a hollow interior 42. The connecting link 31 includes a bottom side 47 (which is a closed top end of the hollow interior 42) that is connected to the (inner) side 49 of the connecting link via two (different) chamfers 41*a* and 41*c*. More about the chamfers is described herein. In one embodiment, the side 49 is the inner cylindrical portion of the hollow interior 42 that extends from both chamfers to the opening 44 along the Z-axis. The table link 32 is a structure that is at least partially cylindrically-shaped. The link 32 includes a top side 46 that is connected to a (outer) side 48 via two (different) chamfers 41b and 41d. More about the chamfers is described herein. In one embodiment, the side 48 is a cylindrical portion of the table link 32 that at least partially extends below both chamfers along the Z-axis.

As shown, the connecting link 31 is being coupled to the table link 32. Specifically, the connecting link is being moved towards the table link (along the Z-axis) to be seated on top of the table link (as illustrated by a downward arrow). Specifically, the connecting link is a female-type connector that fits over the table link that is a male-type connector. Thus, the opening 44 (and the hollow interior 42) are configured to receive the table link. When coupled to the table link, an inner surface 43 (of the hollow interior 42) of the connecting link conforms to at least a portion of an outer surface 45 of the table link. In one embodiment, the inner surface 43 may be the surface of at least one of the inner side 49, chamfers 41a and 41c, and bottom side 47, while the outer surface 45 may be the surface of at least one of the outer side 48, chamfers 41b and 41d, and top side 46. This figure, however, illustrates the magnetic latch 25, before the connecting link is fully coupled (or seated on) the table link. In one embodiment, the links may have a reverse configuration. For example, the table link 32 may be the female-type connector that is configured to receive the connecting link, which is a male-type connector.

As described above, the table link 32 is at least partially cylindrically-shaped and the connecting link 31 is at least partially tubular shaped, having a hollow interior therein. In this case, the opening 44 of the connecting link 31 has a diameter that is at least (or more than) a (e.g., outer) diameter of at least a portion of the table link 32 (e.g., a diameter of the side 48, below chamfer 41d) in order to allow the connecting link to fit over the table link. In another embodiment, either of the links may be shaped differently, for example each of the links may be cubic-shaped, where one link has an opening that is configured to receive at least a portion of the other link.

The magnetic latch 25 also includes a (first) interconnecting mechanism 39 and a (second) interconnecting mechanism 40 that is different than the first interconnecting mechanism, both of which are configured to prevent the magnetic latch from rotating when the robotic arm is coupled to the surgical table. Both of the mechanisms include different pairs of chamfers (or beveled edges) that are sized to mate together. In particular, the first interconnecting mechanism includes a (first) chamfer 41a and a (second) chamfer 41b. Chamfer 41a is a beveled edge having an angle $\theta_1$, and being between (at least a portion of) the bottom side 47 and (at least a portion of) the side 49 within the hollow interior 42. Chamfer 41b is also a beveled edge having an angle $\theta_2$, and being between (at least a portion of) the top side 46 of the table link 32 and (at least a portion of) the side 48 of the table link. Both chamfers are sized (or angled) such that they mate together when the connecting link is coupled to the table link. Thus, both angles $\theta_1$ and $\theta_2$ may equal 360°. For example, $\theta_1$ may equal 135°, while $\theta_2$ is 225°. In one embodiment, $\theta_1$ may be less than or equal to 180° and $\theta_2$ may be greater than or equal to 180°. In another embodiment, the angles may be different.

Similarly, the second interconnecting mechanism includes a (third) chamfer 41c and a (fourth) chamfer 41d. Chamfer 41c is a beveled edge having an angle $\theta_3$, and being between (at least a portion of) the bottom side 47 and (at least a portion of) the side 49 within the hollow interior 42. Chamfer 41d is also a beveled edge having an angle $\theta_4$, and being between (at least a portion of) the top side 46 of the table link 32 and (at least a portion of) the side 48 of the table link. Similar to chamfers 41a and 41b, chamfers 41c and 41d may be sized (or angled) such that they mate together when the connecting link is coupled to the table link.

As described above, the second interconnecting mechanism is different than the first interconnecting mechanism. In one embodiment, the angles $\theta_3$ and $\theta_4$ of the second mechanism 40 may be different than angles $\theta_1$ and $\theta_2$ of the first mechanism 39. For example, $\theta_3$ may be 120°, while $\theta_1$ may be 140°. As a result, the chamfers of the table link would have different angles as well. In this example, $\theta_4$ would be 240° and $\theta_2$ would be 220°. In another embodiment, the length of the chamfers (e.g., a distance between two sides between which a chamfer is positioned) may also be different. For instance, chamfers 41a and 41b may have a first length (e.g., one inch), while chamfers 41c and 41d may have a second length (e.g., two inches). As a result, the chamfers of the first interconnecting mechanism 39 are not sized to mate with chamfers of the second interconnecting mechanism 40. In particular, chamfer 41a is not sized to mate with chamfer 41d, and chamfer 41c is not sized to mate with chamfer 41b. Thus, by having different interconnecting mechanisms, the robotic arm 4 may only be coupled to the surgical table in one position, where the chamfers of the connecting link match up with corresponding chamfers of the table link. This ensures that the connecting link 31 of the arm is coupled correctly to the table link.

As described herein, the different interconnecting mechanisms may prevent the connecting link 31 from rotating while coupled to the table link 32 (about the Z-axis). In one embodiment, the chamfers of both links may be beveled edges between different portions of the links, respectively. Specifically, chamfers 41a and 41c may be beveled edges along different non-overlapping radial segments within the hollow interior about the Z-axis. Similarly, chamfers 41b and 41d may be beveled edges along different non-overlapping radial segments of the table link about the Z-axis. As a result, when the connecting link is coupled to the table link, it is prevented from rotating due to different radial segments of both links having different beveled edges.

In one embodiment, the magnetic latch 25 may only include one interconnecting mechanism (e.g., mechanism 39). In another embodiment, the latch may include two or more interconnecting mechanisms, where each mechanism is different from the other mechanisms.

Continuing with FIG. 3, the (e.g., connecting link 31 of the) magnetic latch 25 includes a ferromagnetic plate 33 and two (first) connectors 34. In one embodiment, the ferromagnetic plate may be composed of any type of ferromagnetic material (e.g., iron). In another embodiment, the plate may be any shape and size. For instance, in this example the plate is disc-shaped. The plate, however, may be bar-shaped. In some embodiments, the connecting link 31 may include one or more plates.

The two connectors 34 are each (e.g., electrically) coupled to one or more components (e.g., a processor, an actuator, etc.) of the robotic arm and are configured to provide at least one of 1) robotic control commands from the control tower 3 to the robotic arm and 2) power to the one or more components of the robotic arm. As described herein, the connectors 34 may be configured to provide the commands and power when coupled to respective connectors 35 of the table link 32 when the robotic arm 4 is magnetically coupled to the surgical table 5, as described herein. In this figure, the connectors 34 are male-type connectors. In one embodiment, the magnetic latch 25 may include only one connector 34. In another embodiment, the latch may include more than two connectors.

The (e.g., table link 32 of the) magnetic latch 25 includes a permanent magnet 48, a canceling coil 37, two connectors 35, and a controller 36. In one embodiment, the table link may have more or less components. For example, the table link may have more than two connectors, may not include a canceling coil 37, or may only have one connector. The connectors 35 may be (e.g., electrically) coupled to the control tower 3 (e.g., via a wired or wireless connection). One or more of the connectors may also be electrically coupled to a power source (e.g., a battery). In one embodiment, the table link 32 includes a same number of connectors 35 as connectors 34 in the connecting link 31. In one embodiment, connectors 34 of the connecting link are configured to come into contact with the connectors 35 of the table link when the robotic arm couples to the surgical table. For instance, the connectors 35 may be female-type connectors that are configured to receive connectors 34 when the connecting link couples to the table link.

In one embodiment, the connectors 34 and/or 35 may be located at different locations. For instance, at least one of the connectors 34 may be on the inner side 49 and at least one of the connectors 35 may be on the outer side 48. When the connecting link 31 is mounted upon the table link both connectors may come into contact with one another. In another embodiment, the at least one of the connectors may be on an outside surface of the connecting link (or robotic arm). In this case, a user may connect a corresponding connector of the table link (or of the table) via a wire.

The permanent magnet (or magnet) 48 is an object made from a material (e.g., a ferromagnetic material) that is magnetized and produces (or creates) its own persistent (first) magnetic field. In this example, the magnet is ring-shaped and is formed (or integrated) within the cylindrically-shaped table link 32 and about the Z-axis (which runs perpendicularly through a center axis of the ring). In one embodiment, the magnet may have any shape (e.g., a bar magnet). In another embodiment, the table link may include two or more permanent magnets. As described herein, the magnet produces the first magnetic field and attracts the ferromagnetic plate to thereby couple the robotic arm 4 to the surgical table 5. More about the permanent magnet and its interaction with the ferromagnetic plate is described in FIGS. 4 and 5.

The canceling coil 37 is an object that is configured to produce, when energized, a (second) magnetic field that opposes the first magnetic field produced by the magnet 38. In one embodiment, the canceling coil 37 may be an electromagnet that includes at least a coil of wire wrapped around a core of ferromagnetic material (e.g., iron). When energized, meaning when a current is supplied to the wire, the core produces the second magnetic field. Once current is removed, the canceling coil stops producing the second magnetic field. In one embodiment, the canceling coil may be any type of electromagnet. Thus, the canceling coil may produce (e.g., based on which way current is flowing through the wire) the second magnetic field that may flow in an opposite direction to that of the first magnetic field. As a result, the first magnetic field may be canceled or reduced. Thus, as described herein, the cancelling coil, which when energized, produces the second magnetic field that opposes the first magnetic field to thereby uncouple the robotic arm from the surgical table. In this figure, the canceling coil is ring-shaped, similar to the permanent magnet. In another embodiment, the canceling coil may be any shape (e.g., bar-shaped). Also, there are may two or more canceling coils that may be independently energized and unenergized. More about the canceling coil is described in FIG. 5.

The controller 36 may be a special-purpose processor such as an application-specific integrated circuit (ASIC), a general purpose microprocessor, a field-programmable gate array (FPGA), a digital signal controller, or a set of hardware logic structures (e.g., filters, arithmetic logic units, and dedicated state machines). In one embodiment, the controller may also include memory. As illustrated, the controller 36 is a part of the table link 32. In one embodiment, the controller may be separate from the table link 32. For example, the controller may be a part of or integrated with table-side electronics (not shown) of the surgical table. As another example, the controller may be a part of the control tower 3 and/or the computer system 16.

As shown, the controller 36 is coupled (e.g., via wires) to the canceling coil 37 and is configured to energize (e.g., provide current to) the canceling coil 37 and unenergize (e.g., cease providing current to) the canceling coil. In one embodiment, the controller is configured to energize and unenergize the canceling coil based on received input. As one example, the input may be user input received via a button (not shown) when user-actuated by a user. In this example, the button may be a part of the surgical table 5, such as being on the adapter 22 or the table link 32. When the user wishes to remove a robotic arm, the button may be pressed, thereby instructing the controller to energize the canceling coil. In one embodiment, the controller may energize the canceling coil for a period of time after receiving input (e.g., ten seconds), in order to allow the user to remove the robotic arm with both hands. Once the time has passed, the canceling coil may be unenergized. As another example, the input may be received from the UID 14 that is being operated by the operator 9. As yet another example, the input may be sensor data obtained by one or more sensors (not shown). Specifically, the table link (or the connecting link 31) may include one or more proximity sensors, when the proximity sensors detect that an object is within a threshold distance, which may represent the connecting link being placed atop the table link, the controller may unenergize the coil (if currently being energized). In another embodiment, the magnetic latch 25 may include one or more strain gauges that are configured to detect when a user is pulling on the robotic arm. If detected, the controller may energize the canceling coil in order to allow the user to uncouple the robotic arm from the table link 32.

In one embodiment, the magnetic latch 25 may have different configurations of at least some of the components described herein. For example, the ferromagnetic plate 33 and the canceling coil 37 may be integrated with the table link 32, and the permanent magnet 38 may be integrated with the connecting link 31. As another example, the permanent magnet and the cancelling coil may be integrated with the connecting link, while the plate 33 is integrated with eh table link. In yet other configurations, each link may include some the same components. For instance, both links may include at least one of the same components (e.g., both having one or more plates 33). In one embodiment, the placement of the components may be different than illustrated in this figure. For example, one or more ferromagnetic plates may be integrated along the side 49 of the connecting link 31, while one or more permanent magnets 38 (and one or more canceling coils 37) are integrated along the side 48 of the table link.

Figure 4:
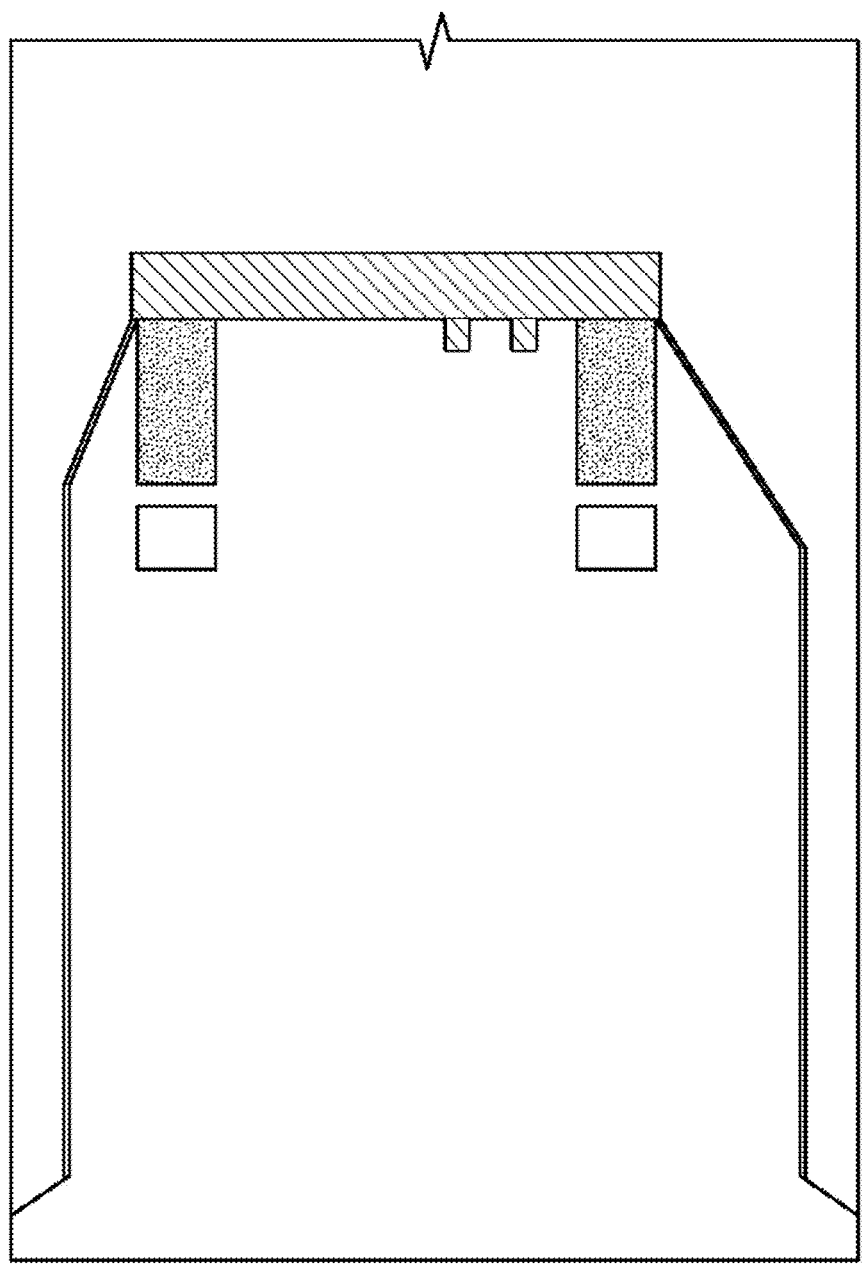
FIG. 4 shows a cross-sectional view of the magnetic latch in which the robotic arm is magnetically coupled to the surgical table according to one embodiment.

FIG. 4 shows a cross-sectional view of the magnetic latch in which the robotic arm is magnetically coupled to the surgical table according to one embodiment. Specifically, this figure illustrates that the connecting link 31 is coupled to the table link 32, and being held in place by the first magnetic field being produced by the permanent magnet 38. Thus, the permanent magnet creates an axial bond with the ferromagnetic plate in order to couple the (connecting link of the) robotic arm 4 to the surgical table. This axial bond is automatically created due to the persistent magnetic field produced by the permanent magnet being attracted to the ferromagnetic plate of the connecting link. Thus, the inner surface 43 of the connecting link is seated atop the outer surface 45 of the table link 32. Also illustrated, the chamfers of the connecting link are seated on respective chamfers of the table link, and the first connectors 34 are in contact with and is received by the second connectors 35. Since the two pairs of connectors are in contact with each other, the robotic arm may be operational (e.g., receiving robotic commands and power), immediately after the robotic arm is magnetically coupled to the surgical table, without requiring the user to perform any additional tasks (e.g., plugging in wires or connectors).

Figure 5:
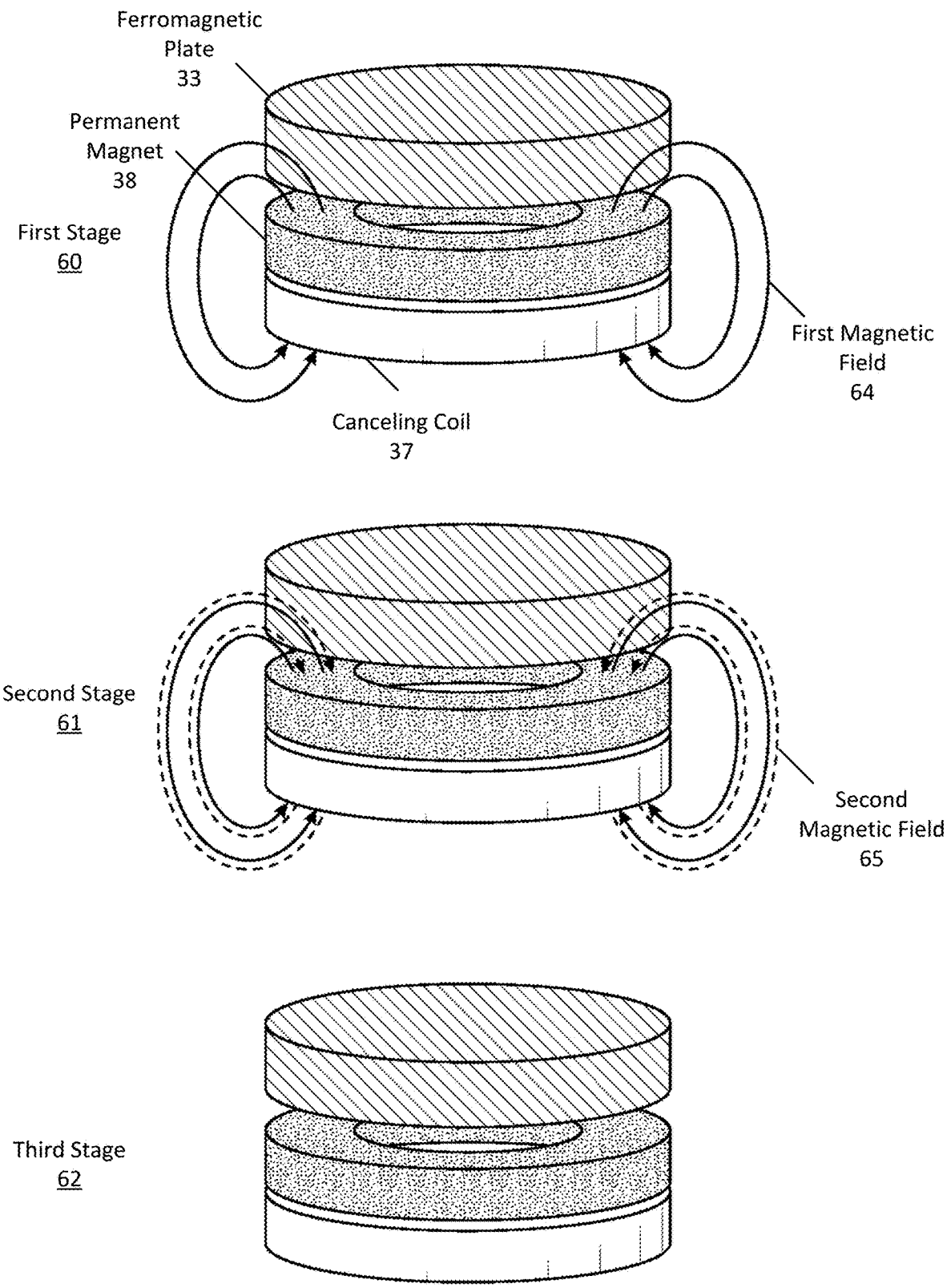
FIG. 5 shows several stages in which a canceling coil of the magnetic latch begins to produce an opposing magnetic field to that of the permanent magnet in order to uncouple the robotic arm according to one embodiment.

FIG. 5 shows several stages in which a canceling coil of the magnetic latch begins to produce an opposing magnetic field to that of the permanent magnet in order to uncouple the robotic arm according to one embodiment. Specifically, this figure illustrates three stages 60-62, that illustrate the magnetic fields produced by the permanent magnet 38 and the canceling coil 37 of the magnetic latch 25.

Stage 60 shows the permanent magnet 38 producing the first magnetic field, illustrated as flux lines 64 that flow from the top of the permanent magnet, through the plate 33, and around the bottom of (the canceling coil 37 and) the magnet. Thus, this stage represents that the magnetic latch is magnetically coupling the robotic arm 4 to the surgical table 5. As a result of the production of the first magnetic field, the plate (and therefore the robotic arm) is held in place.

Stage 61 shows the canceling coil 37 being energized (e.g., by the controller 36) and as a result is producing the second magnetic field that is opposing the first magnetic field. Specifically, the second magnetic field is illustrated as flux lines 65 that flow in the opposite direction than the flux lines 64 of the first magnetic field.

Stage 62 shows the result of the canceling coil 37 being energized. Specifically, the opposing second magnetic field cancels or reduces the first magnetic field, as illustrated by both flux lines not being illustrated. In one embodiment, at least a portion of the first magnetic field (and the second magnetic field) may still be present. For instance, the first magnetic field may be present, but as a result of the opposing second magnetic field may be greatly reduced. As a result, at this point the (surgical arm containing the) plate is still coupled to the surgical table, but may be uncoupled by pulling up on the arm to cause the plate to move away from the magnet 38.

Figure 6:
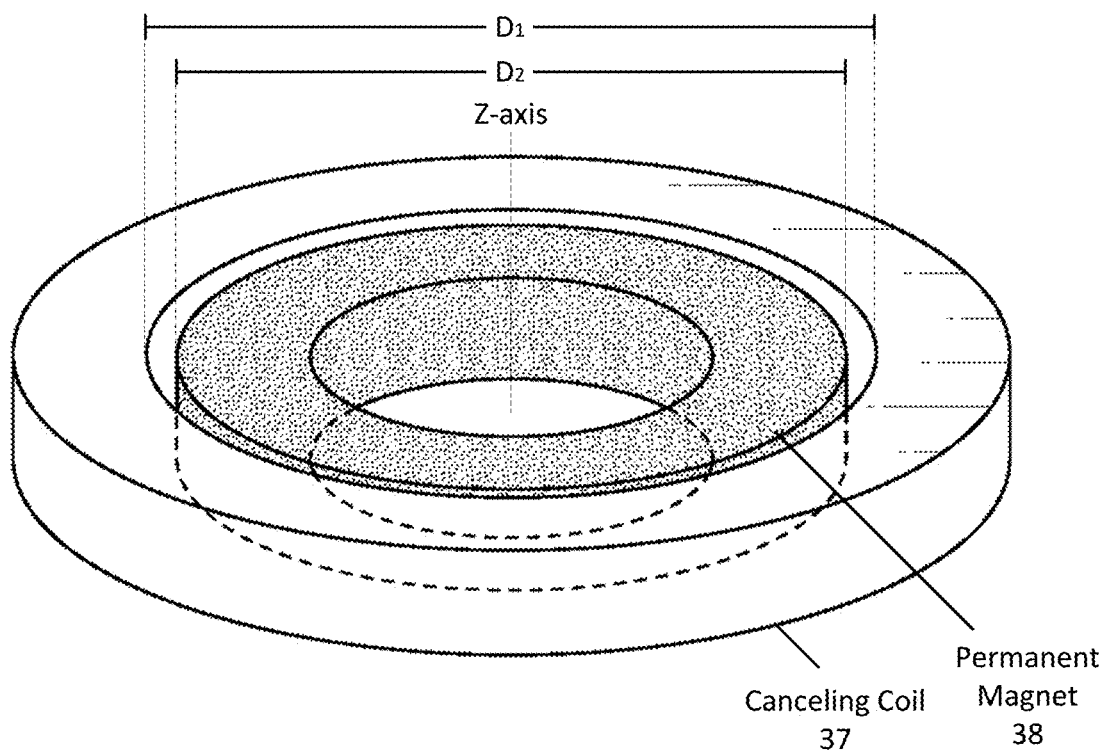
FIG. 6 shows an example of an arrangement of the permanent magnet and the cancelling coil of the magnetic latch according to one embodiment.
Figure 7:
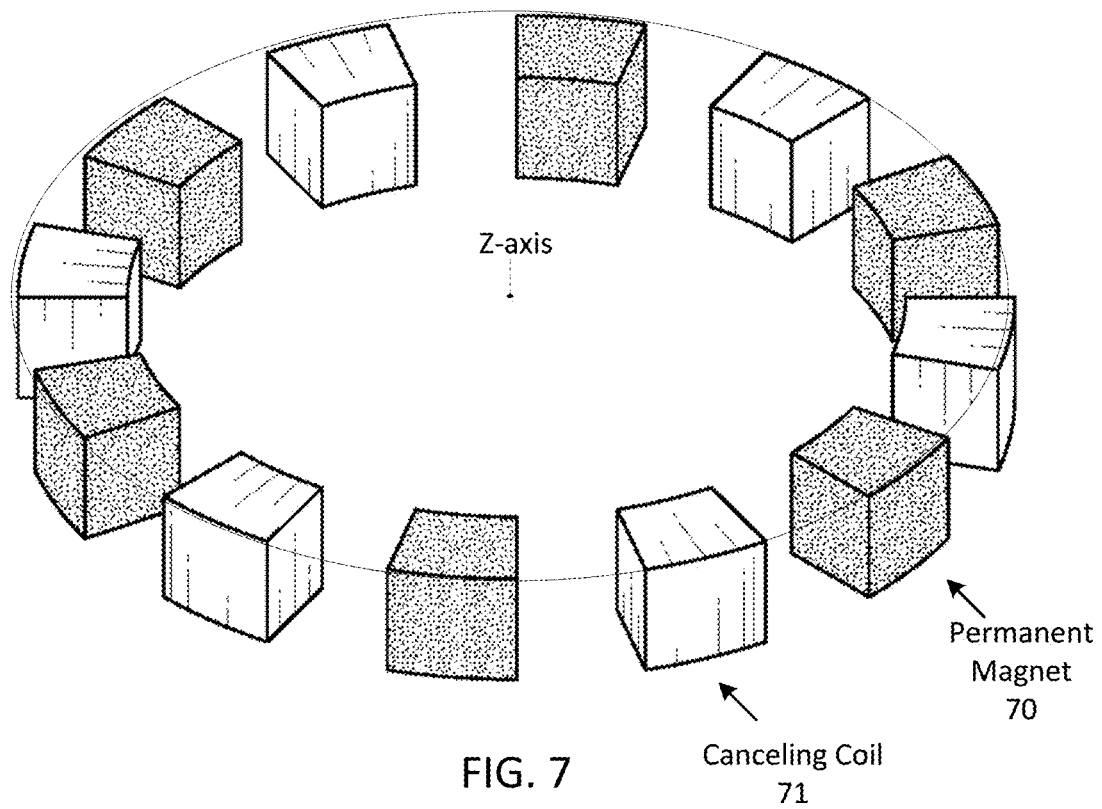
FIG. 7 shows an example of another arrangement of several permanent magnets and several canceling coils of the magnetic latch according to one embodiment.

FIGS. 6 and 7 show examples of different arrangements of the permanent magnet and the canceling coil of the magnetic latch according to some embodiments. For instance, as described herein, the permanent magnet 38 and the canceling coil 37 may both be ring-shaped, where one is disposed on top of the other (as illustrated in FIG. 5). Other arrangements, however, are possible. For example, FIG. 6 illustrates an arrangement in which the permanent magnet is disposed inside (e.g., a hollow portion) of the canceling coil. Specifically, the canceling coil has an inner (first) diameter $D_1$ and the permanent magnet has an outer (second) diameter $D_2$, where $D_2$ is less than $D_1$. Each of the components are longitudinally aligned with a center Z-axis. Thus, the permanent magnet is inside the canceling coil and is radially aligned with the canceling coil about the Z-axis that runs through the center of both components. In one embodiment, each of the components may have the same height, such that a top and bottom side of both components are radially aligned with one another. In another embodiment, either component may have a different height with respect to the other. For example, the canceling coil may be disposed higher than the permanent magnet along the Z-axis.

FIG. 7 illustrates an arrangement in which the magnetic latch includes several permanent magnets and several canceling coils. Specifically, this figure illustrates six magnets 70 and six coils 71 that are arranged in a circular fashion about the Z-axis. Each of the magnets and coils is illustrated as a cube. In one embodiment, the magnets and coils may be any shape (e.g., cylindrical). As illustrated, the magnets and coils are arranged such that the magnets are evenly spaced apart along an inner circumference of a circle with a center through which the Z-axis runs. Each of the canceling coils is positioned between different pairs of adjacent permanent magnets. In other words, between every two permanent magnets is a canceling coil. Each of the coils and magnets may have a same (or similar) radial distance from the Z-axis. In one embodiment, such an arrangement may be integrated into either the table link or the connecting link. In another embodiment, some of the components may be distributed between the connecting link 31 and the table link 32. For instance, the coils may be a part of the connecting link, while the magnets are a part of the table link. Thus, the coils may be disposed higher than the permanent magnets along the Z-axis.

In one embodiment, each of the canceling coils 71 may be energized independently with respect to one another. For example, at least some may be redundant canceling coils that are only energized when other canceling coils are inoperable.

Figure 8:
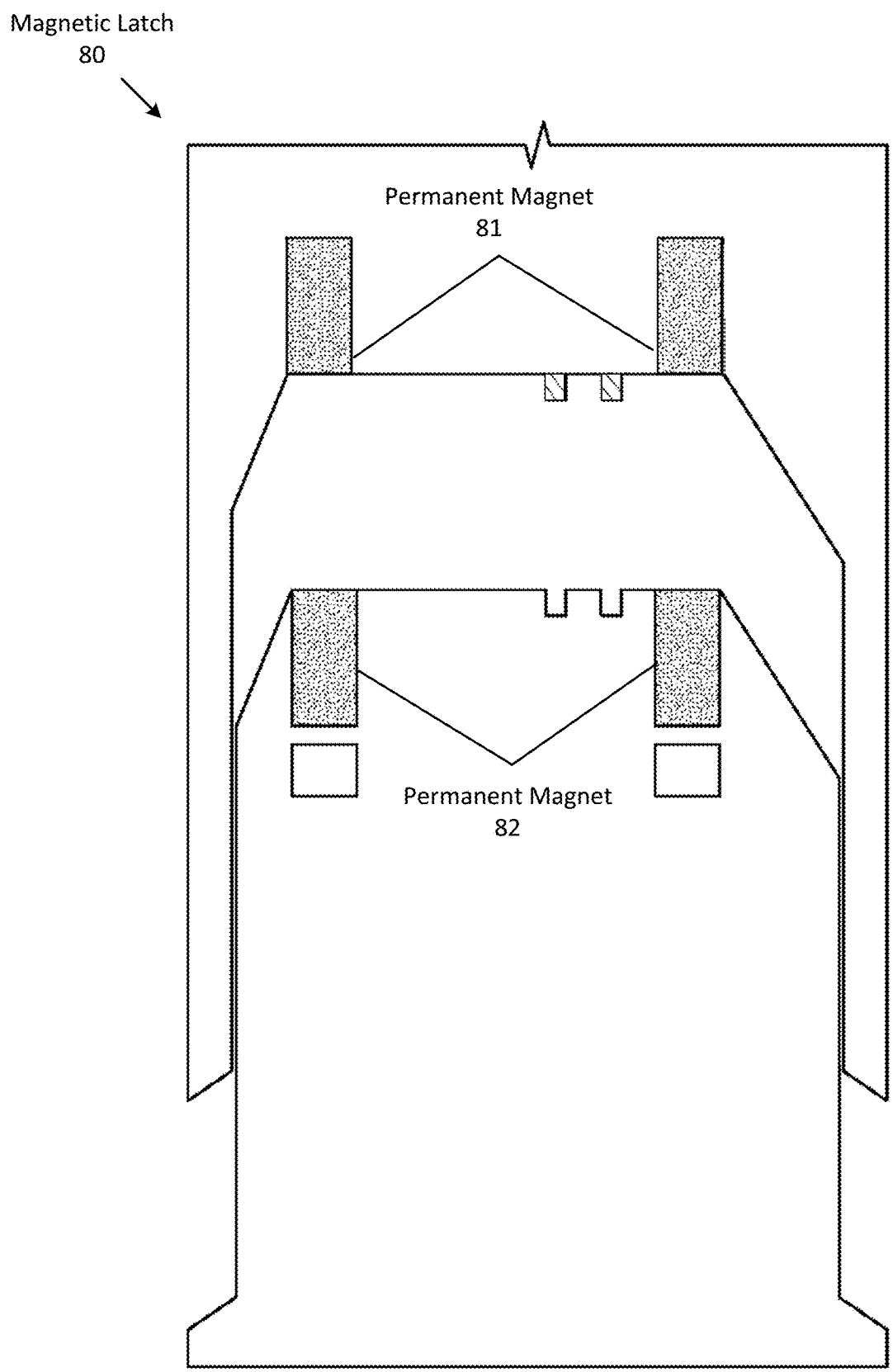
FIG. 8 shows an example of the magnetic latch that is coupling the robotic arm to the surgical table of the robotic system according to one embodiment.

FIG. 8 shows an example of the magnetic latch that is configured to couple a robotic arm to the surgical table of the robotic system according to one embodiment. This figure illustrates a magnetic latch 80 that does not include a ferromagnetic plate 33, as illustrated in the magnetic latch 25 in FIG. 3. Instead, the magnetic latch 80 includes a (first) permanent magnet 81 that is integrated with the connecting link 31 and a (second) permanent magnet 82 that is integrated with the table link 32 (along with the canceling coil. In one embodiment, the arrangement may be different, as described herein. For example, the first permanent magnet 81 and the canceling coil may be integrated with the connecting link 31, and the second permanent magnet 82 may be integrated with the table link 32. In either case, the first magnet produces a first magnetic field and the second magnet produces a second magnetic field, both magnets attract one another to thereby magnetically couple the robotic arm to the surgical table. Thus, both magnets produce similar flowing magnetic fields, which as a result attract each other. In one embodiment, both magnets are the same or they may be different, meaning that one magnet may produce a stronger magnetic field than the other. This may be the case with respect to the connecting link. In particular, the size (e.g., weight) of the magnet corresponds to the strength of its magnetic field. Therefore, in order to minimize the weight of the robotic arm, the second magnet may be heavier (and therefore stronger) than the first magnet, which is disposed within the connecting link of the robotic arm.

In this case, the canceling coil, which when energized, produces a (third) magnetic field that opposes at least one of the first and second magnetic fields produced by the first and second magnets, respectively, to thereby uncouple the robotic arm from the surgical table. In one embodiment, since both magnetic fields produced by the first and second magnets have similar flowing magnetic fields, the canceling coil may cancel or reduce both magnetic fields. In one embodiment, both links may include at least one canceling coil in order to counteract the magnetic fields.

As previously explained, an embodiment of the disclosure may be a non-transitory machine-readable medium (such as microelectronic memory) having stored thereon instructions, which program one or more data processing components (generically referred to here as a "processor") to determine whether one or more canceling coils should be energized or unenergized. In other embodiments, some of these operations might be performed by specific hardware components that contain hardwired logic. Those operations might alternatively be performed by any combination of programmed data processing components and fixed hardwired circuit components.

While certain embodiments have been described and shown in the accompanying drawings, it is to be understood that such embodiments are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some embodiments, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some embodiments, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. A surgical robotic system comprising:
    a surgical table that is configured to hold a patient; and
    a magnetic latch having
        a ferromagnetic plate,
        a permanent magnet that produces a first magnetic field and that attracts the ferromagnetic plate to thereby couple a robotic arm to the surgical table, and
        a canceling coil, which when energized, produces a second magnetic field that opposes the first magnetic field to thereby uncouple the robotic arm from the surgical table.

2. The surgical robotic system of claim 1, wherein the magnetic latch comprises a connecting link of the robotic arm and a table link that is rigidly coupled to the surgical table, which are configured to latch together.

3. The surgical robotic system of claim 2, wherein the permanent magnet and the canceling coil are integrated with of the table link, and the ferromagnetic plate is integrated with the connecting link.

4. The surgical robotic system of claim 2, wherein the ferromagnetic plate and the canceling coil are integrated with the table link, and the permanent magnet is integrated with the connecting link.

5. The surgical robotic system of claim 2, wherein the connecting link has a first connector and the table link has a second connector, wherein the first connector of the connecting link is configured to come into contact with the second connector of the table link when the robotic arm couples to the surgical table.

6. The surgical robotic system of claim 1, wherein the magnetic latch further has a first interconnecting mechanism and a second, different interconnecting mechanism, wherein both mechanisms prevent the magnetic latch from rotating when the robotic arm is coupled to the surgical table.

7. The surgical robotic system of claim 6, wherein the first interconnecting mechanism includes a first pair of chamfers that are sized to mate together and the second interconnecting mechanism includes a second pair of chamfers that are sized to mate together, wherein chamfers of the first pair of chamfers are not sized to mate with chamfers of the second pair of chamfers.

8. A surgical robotic system comprising:
    a surgical table that is configured to hold a patient;
    a robotic arm that includes a connecting link with a ferromagnetic plate; and
    a table link that is rigidly coupled to the surgical table and includes
        a permanent magnet that produces a first magnetic field and attracts the ferromagnetic plate to thereby magnetically couple the connecting link of the robotic arm to the table link and
        a canceling coil, which when energized, produces a second magnetic field that opposes the first magnetic field to thereby allow the connecting link to be uncoupled from the table link.

9. The surgical robotic system of claim 8, wherein the connecting link has a first connector and the table link has a second connector, wherein the first connector of the connecting link is configured to come into contact with the second connector when the connecting link of the robotic arm magnetically couples to the table link.

10. The surgical robotic system of claim 8, wherein the connecting link has a first chamfer and the table link has a second chamfer, wherein both chamfers are sized to mate together when the connecting link couples to the table link.

11. The surgical robotic system of claim 10, wherein the connecting link has a third chamfer and the table link has a fourth chamfer, wherein the third and fourth chamfers are sized to mate together when the connecting link couples to the table link.

12. The surgical robotic system of claim 11, wherein the first and fourth chamfers are not sized to mate together and the second and third chamfers are not sized to mate together when the connecting link couples to the table link.

13. The surgical robotic system of claim 8, wherein the permanent magnet is one of a plurality of permanent magnets that are a part of the table link, and the canceling coil is one of a plurality of canceling coils that are a part of the table link, wherein the plurality of permanent magnets and the plurality of canceling coils are arranged in a circular fashion.

14. The surgical robotic system of claim 13, wherein the plurality of permanent magnets and the plurality of canceling coils are arranged in the circular fashion such that the plurality of permanent magnets are evenly spaced apart along a circumference of a circle and each of the plurality of canceling coils is positioned between a different pair of adjacent permanent magnets.

15. The surgical robotic system of claim 8, wherein the permanent magnet and the canceling coil are both ring-shaped.

16. The surgical robotic system of claim 15, wherein the canceling coil has a first diameter and the permanent magnet has a second dimeter that is less than the first diameter.

17. The surgical robotic system of claim 16, wherein the permanent magnet is inside the canceling coil and is radially aligned with the canceling coil about a longitudinal axis that runs through a center of the permeant magnet and the canceling coil.

18. A surgical robotic system comprising:
a surgical table that is configured to hold a patient;
a magnetic latch configured to couple a robotic arm to the surgical table, the magnetic latch has
a first permanent magnet that produces a first magnetic field and a second permanent magnet that produces a second magnetic field, both permanent magnets attract one another to thereby magnetically couple the robotic arm to the surgical table, and
a canceling coil, which when energized, produces a third magnetic field that opposes at least one of the first and second magnetic fields produced by the permanent magnets to thereby uncouple the robotic arm from the surgical table.

19. The surgical robotic system of claim 18, wherein the magnetic latch comprises a connecting link of the robotic arm and a table link that is rigidly coupled to the surgical table.

20. The surgical robotic system of claim 19, wherein
the first permanent magnet is integrated with the connecting link and the second permanent magnet and the canceling coil are integrated with the table link, or
the first permanent magnet and the canceling coil are integrated with the connecting link and the second permanent magnet is integrated with the table link.

* * * * *